(12) United States Patent
Cho et al.

(10) Patent No.: US 12,263,154 B2
(45) Date of Patent: Apr. 1, 2025

(54) COMPOSITION USING 4',6,7-TRIMETHOXYISOFLAVONE AND CATECHOL FOR MANAGING PULMONARY FIBROSIS

(71) Applicant: A-CHEMBIO CO., LTD, Gyeonggi-do (KR)

(72) Inventors: Moon Jae Cho, Jeju-do (KR); Young Mee Kim, Jeju-do (KR); Bong Jo Son, Jeju-do (KR)

(73) Assignee: A-CHEMBIO CO., LTD, Gyeonggi-do (KR)

( * ) Notice: Subject to any disclaimer, the term of this patent is extended or adjusted under 35 U.S.C. 154(b) by 750 days.

(21) Appl. No.: 17/612,712

(22) PCT Filed: Jul. 6, 2021

(86) PCT No.: PCT/KR2021/008552
§ 371 (c)(1),
(2) Date: Nov. 19, 2021

(87) PCT Pub. No.: WO2022/010219
PCT Pub. Date: Jan. 13, 2022

(65) Prior Publication Data
US 2022/0218655 A1    Jul. 14, 2022

(30) Foreign Application Priority Data

Jul. 8, 2020    (KR) .................. 10-2020-0084225

(51) Int. Cl.
*A61K 31/352*    (2006.01)
*A61K 31/05*    (2006.01)
*A61P 11/00*    (2006.01)

(52) U.S. Cl.
CPC ............ *A61K 31/352* (2013.01); *A61K 31/05* (2013.01); *A61P 11/00* (2018.01)

(58) Field of Classification Search
CPC .............................. A61K 31/05; A61K 31/352
See application file for complete search history.

(56) References Cited

PUBLICATIONS

Kim et al. (Lung (2006) 184:287-295).*
Melak et al. (Natural Science (2013) vol. 5, No. 8, 888-894).*

* cited by examiner

*Primary Examiner* — Valerie Rodriguez-Garcia
(74) *Attorney, Agent, or Firm* — Harness, Dickey & Pierce, P.L.C.

(57) ABSTRACT

Proposed is a composition for managing pulmonary fibrosis. The composition uses 4',6,7-trimethoxyisoflavone and catechol that does not cytotoxicity and inhibits a TGF-β1 signal transfer pathway, thereby exhibiting EMT inhibitory activity.

3 Claims, 9 Drawing Sheets

COMPOSITION USING 4',6,7-TRIMETHOXYISOFLAVONE AND CATECHOL FOR MANAGING PULMONARY FIBROSIS

CROSS-REFERENCE TO RELATED APPLICATIONS

This application is a National Phase entry of PCT Application No. PCT/KR2021/008552, filed 6 Jul. 2021 which claims priority to Korean Patent Application No. 10-2020-0084225, filed 8 Jul. 2020. The entire disclosure of the application identified in this paragraph is incorporated herein by reference.

TECHNICAL FIELD

The present disclosure relates to a composition using 4',6,7-trimethoxyisoflavone and catechol for managing pulmonary fibrosis.

BACKGROUND

Pulmonary fibrosis or idiopathic pulmonary fibrosis (IPF) is a disease characterized by fibrosis of the lung interstitium in which connective tissue, particularly collagen, is excessively engrafted in the alveolar wall. Pulmonary fibrosis is a fatal disease that progresses to respiratory failure due to a gradual decline in lung function and has an average survival period of less than 2-3 years after diagnosis. The prevalence of pulmonary fibrosis varies from report to report, but it is known to be 2-29 out of 100,000 people and is designated as a rare and intractable disease in Korea.

Pulmonary fibrosis is a disease that occurs in the elderly and is expected to increase gradually as the population ages. Recent research results have reported that the prevalence of pulmonary fibrosis reported to date is underestimated, reporting that about 7-8% of smokers or the general population. Therefore, it is expected that a considerable number of older people (currently, 1 in 450 men over 70 years of age) will suffer from this disease, but there is still no effective treatment method. Lung transplants also require a long waiting time because the number of transplant donors is smaller than the number of patients who need to receive a transplant (so many of the patients come to death while waiting for a transplant because the disease continuously worsens). Even if the patients fortunately receive a lung transplant, many of them fail to survive due to complications after the transplant (5-year survival rate is about 50%). Therefore, a more effective and safe treatment method is urgently needed.

The causes of pulmonary fibrosis are diverse, including lung damage, exposure to toxic substances or toxic environments such as fine dust or ultrafine dust, anticancer drugs, autoimmune diseases, or idiopathic interstitial pneumonia (Proc Am Thorac Soc). 2006, 3:285-92; Am J Respir Crit Care Med 2002, 165:277-304). The basic histological changes in pulmonary fibrosis include inflammatory changes such as cell infiltration, edema, and exudation in the alveolar septum and the destruction of lung parenchymal by infiltration and fibrosis of extracellular matrixes such as collagen, proteoglycan, fibronectin, and glycoprotein (Am J Respir Crit Care Med 2002, 165:277-304; N Engl J Med 2001, 345:517-25).

In the past, anti-inflammatory treatment was attempted by seeing the etiology of pulmonary fibrosis as inflammation, but the actual effect was insignificant (Annals of Internal Medicine 2001, 134:136-51; Chest 1996, 110:1058-67). TGF-β1 signaling leading to epithelial-mesenchymal transition (EMT) or EMT is being addressed as new pathogenesis and therapeutic goal (Annals of Internal Medicine 2001, 134:136-51; Chest). 2007, 132:1311-21; The Journal of Clinical Investigation 2009, 119:213-24).

The main factor inducing EMT is TGF-β1. TGF-β1 induces the neogenesis of α-SMA (α-Smooth muscle actin) during EMT, and the neogenesis of α-SMA changes lung fibroblasts into myofibroblast phenotype. The expression of these myofibroblasts is estimated to play a major role in the development and progression of pulmonary fibrosis because the expression of these myofibroblasts is upregulated and continuously expressed at the site where lung fibrosis is progressing (Chest 2002,122:286S-9S).

In particular, it is known that the expression of α-SMA, vimentin, fibronectin, and SMA2/3 is increased in association with the TGF-β pathway, and E-cadherin is converted to N-cadherin, promoting EMT and causing pulmonary fibrosis (The Journal of Clinical Investigation 2009,119:213-24; Nat Rev Mol Cell Biol 2006,7:131-42; Cell Biol Int 2002,26:463-76). In addition, it is known that the Smad-dependent pathway and the Smad-independent mitogen-activated protein kinases (MAPK) pathway are involved in a cell by TGF-β1 (J Am Soc Nephrol 2002, 13:1464-72; Proc Natl Acad Sci USA 2001, 98:6686-91; Cancer Res 2001;61:4222-8).

Steroids, immunosuppressive agents, and anti-viral cytokines are typically used to treat pulmonary fibrosis, but according to the 2011 ATS/ERS Guidelines for Idiopathic Pulmonary Fibrosis, steroids and combination therapy with the immunosuppressant azathioprine has been shown to increase mortality.

The present disclosure discloses the activity of managing the pulmonary fibrosis of 4',6,7-trimethoxyisoflavone (4',6,7-trimethoxyisoflavone) and catechol (1,2-dihydroxybenzene) having EMT inhibitory activity by inhibiting the TGF-β1 signal transmission path.

SUMMARY

Technical Problem

The objective of the present disclosure is to provide a composition for managing pulmonary fibrosis using 4',6,7-trimethoxyisoflavone and catechol having EMT inhibitory activity and TGF-β1 signaling pathway inhibitory activity.

Other objectives or specific objectives of the present disclosure will be set forth below.

Technical Solution

The present disclosure was completed by confirming that 4',6,7-trimethoxyisoflavone and/or catechol inhibit TGF-β1 signaling pathway without showing specific cytotoxicity, thereby inhibiting EMT and also showing pulmonary fibrosis inhibitory effects in pulmonary fibrosis animal models, through the Examples and Experimental Examples below.

The present disclosure is based on the results of the experiments described below. In one aspect of the present disclosure, proposed is a composition for managing pulmonary fibrosis, and the composition contains 4',6,7-trimethoxyisoflavone and/or catechol as an active ingredient.

The 4',6,7-trimethoxyisoflavone is a compound present in legumes and the like, and catechol is a compound present in fruits and vegetables. The chemical structural formulae thereof are shown below.

<Formula 1>

4',6,7-trimethoxyisoflavone

<Formula 2>

1,2-dihydroxybenzene

As used herein, the term "active ingredient" refers to a component that may exhibit the desired activity by being used solely or may exhibit the desired activity by being used in conjunction with an inactive carrier.

In the composition of the present disclosure, the active ingredient may be included in a predetermined amount (effective amount) varying depending on the use thereof, formulation, etc., as long as the active ingredient may exhibit the effect of managing pulmonary fibrosis, etc., but the typical effective amount may be 0.001% to 15% by weight relative to the total weight of the composition. Here, the term "effective amount" refers to the amount included in the composition by which the intended medical and pharmacological effects, such as the mitigation of pulmonary fibrosis, can be obtained when the composition is administered to a mammal, preferably a human for a predetermined administration period suggested by a medical professional. Such an effective amount may be determined empirically by the ordinarily skilled in the art.

The composition of the present disclosure may be identified as a food composition in specific embodiments.

The food composition of the present disclosure may be prepared in any form. Specifically, the food composition may be prepared in the form of: beverages such as tea, juice, carbonated beverages, and ionic beverages; processed dairy products such as milk and yogurt; gums; snacks such as rice cakes, Korean sweets, bread, cake and confectionery, and noodles; and health functional food products such as tablets, capsules, pills, granules, liquids, powders, flakes, pastes, syrups, gels, jellies, bars, and the like. In addition, the food composition of the present disclosure may be categorized as any product class according to the legal and functional food classification confirming the enforcement regulations at the time of manufacture and distribution of the composition of the present disclosure. For example, it is a health functional food according to the "Health Functional Food Acts" of Korea, or it may be confectionery, beans, multiples, beverages, or special-purpose foods according to each type of food according to the Food Code of Korea "Korean Food Sanitation Act" (Ministry of Food and Drug Safety Notice "Specifications and Standards of Food ").

The food composition of the present disclosure may additionally contain food additives besides the active ingredient. Food additives are generally understood as substances added to and mixed with or infiltrated into food in manufacturing, processing, or preserving food. Since the food additives will be taken daily and for a long period time along with food, the safety of the food additives must be guaranteed. Safe food additives are limitedly specified in terms of ingredients or functions in the Food Additives Ordinance in accordance with the laws for regulating the manufacture and distribution of food (for example, the "Food Sanitation Act" in Korea) in each country. In the Korean Food Additives Code (Ministry of Food and Drug Safety Notice "Food Additive Standards and Specifications"), food additives are classified into chemically synthetic products, natural additives, and mixed preparations in terms of ingredients. These food additives are classified into sweeteners, flavoring agents, preservatives, emulsifiers, acidulants, thickeners, and the like in terms of functions.

The sweetener is used to impart appropriate sweetness to food, and both natural and synthetic ones may be used in the food composition of the present disclosure. Preferably, a natural sweetener is used. Examples of natural sweetener include sugar sweeteners such as corn syrup solids, honey, sucrose, fructose, lactose, and maltose.

Flavoring agents are used to improve taste or fragrance, and both natural and synthetic ones may be used. Preferably, a natural flavoring agent is used. In the case of using natural ones, and flavor, the purpose of nutritional enhancement may also be combined. The natural flavoring agent may be obtained from apples, lemons, tangerines, grapes, strawberries, peaches, or the like, or obtained from green tea leaves, horseradish leaves, bamboo leaves, cinnamon, chrysanthemum leaves, jasmine, and the like. In addition, those obtained from ginseng (red ginseng), bamboo shoots, aloe vera, ginkgo biloba, etc. may be used. The natural flavoring agent may be a liquid concentrate or a solid extract. In some cases, a synthetic flavoring agent may be used, and the synthetic flavoring agent may include esters, alcohols, aldehydes, terpenes, and the like.

Calcium sorbate, sodium sorbate, potassium sorbate, calcium benzoate, sodium benzoate, potassium benzoate, EDTA (ethylenediaminetetraacetic acid), etc. used as preservatives, and acacia gum, carboxymethylcellulose, xanthan gum, and pectin, and the like may be used as emulsifiers. Citric acid, malic acid, fumaric acid, adipic acid, phosphoric acid, gluconic acid, tartaric acid, ascorbic acid, acetic acid, phosphoric acid, and the like may be used as the acidulant. The acidulant may be added so that the food composition has an appropriate acidity for inhibiting the growth of microorganisms in addition to the purpose of enhancing the taste. As a thickening agent, a suspension implementation agent, a settling agent, a gel-forming agent, a bulking agent, etc., may be used.

The food composition of the present disclosure may contain, in addition to the food additives as described above, bioactive substances or minerals known in the art to supplement and reinforce functionality and nutrition and guaranteed stability as food additives.

Examples of such physiologically active substances include catechins contained in green tea and the like, vitamins such as vitamin B1, vitamin C, vitamin E, and vitamin B12, tocopherol, dibenzoyl thiamine, and the like. As minerals, calcium preparations such as calcium citrate, magnesium preparations such as magnesium stearate, iron preparations such as iron citrate, chromium chloride, potassium iodide, selenium, germanium, vanadium, zinc, etc. are included.

In the food composition of the present disclosure, the food additives as described above may be included in an appropriate amount to achieve the purpose of the addition according to the type of product.

In relation to other food additives that may be included in the food composition of the present disclosure, reference may be made to the Food Ordinance or Food Additives Code according to each country's laws.

The composition of the present disclosure may be regarded as a pharmaceutical composition in another specific embodiment.

The pharmaceutical composition of the present disclosure may be prepared as an oral dosage form or parenteral dosage form according to the route of administration by a conventional method known in the art, including a pharmaceutically acceptable carrier in addition to the active ingredient. Here, "pharmaceutically acceptable" means that it does not inhibit the activity of an active ingredient and does not have toxicity beyond what the application (prescription) target may adapt.

When the pharmaceutical composition of the present disclosure is prepared as an oral dosage form, it may be prepared in a formulation such as powders, granules, tablets, pills, sugar-coated tablets, capsules, liquids, gels, syrups, suspensions, wafers according to methods known in the art together with suitable carriers. In this case, examples of suitable pharmaceutically acceptable carriers include sugars such as lactose, glucose, sucrose, dextrose, sorbitol, mannitol, and xylitol, starches such as corn starch, potato starch, wheat starch, celluloses such as cellulose, methylcellulose, ethylcellulose, sodium carboxymethylcellulose, and hydroxypropyl methylcellulose, polyvinylpyrrolidone, water, methyl hydroxybenzoate, propyl hydroxybenzoate, magnesium stearate, mineral oil, malt, gelatin, talc, polyol, vegetable, and oil. For formulation of the composition, diluents and/or excipients such as fillers, thickeners, binders, wetting agents, disintegrating agents, and surfactants may be used as necessary.

When the pharmaceutical composition of the present disclosure is prepared for parenteral use, it may be formulated in eye drops, injection, transdermal administration, nasal inhalation, or suppository together with a suitable carrier according to methods known in the art. When formulated as eye drops, as a suitable carrier, sterilized water, saline, 5% dextrose, etc., may be used, and benzalkonium chloride, methylparaben, ethyl paraben, etc. be added for preservative purposes as necessary. When formulated as an injection, sterilized water, polyol such as ethanol, glycerol, propylene glycol, or a mixture thereof may be used as a suitable carrier, and preferably an IV solution, a phosphate buffered saline (PBS) containing triethanol amine, an emerging solution such as 5% dextrose may be used. When formulated for transdermal administration, it may be formulated in the form of ointments, creams, lotions, gels, external solutions, pasta agents, liniment agents, air rolls, and the like. In the case of nasal inhalants, suitable propellers such as dichlorofluoromethane, trichlorofluoromethane, dichlorotetrafluoroethane, and carbon dioxide may be used to form an aerosol spray. When formulated as a suppository, Witepsol®, tween 61, polyethylene glycols, cacao oil, laurin oil, polyoxyethylene sorbitan fatty acid esters, polyoxyethylene stearates, sorbitan fatty acid esters, and the like may be used as the base agents.

Specific formulations of pharmaceutical compositions are known in the art, and reference may refer to, for example, Remington's Pharmaceutical Sciences (19th ed., 1995). This document is considered a part of this disclosure.

A preferred dosage of the pharmaceutical composition of the present disclosure may range from 0.001 mg/kg to 10 g/kg per day, preferably 0.001 mg/kg to 1 g, depending on the patient's condition, weight, sex, age, the severity of the patient, and the route of administration. Administration may be performed once a day or divided into several times a day. Such dosages should not be construed as limiting the scope of the disclosure in any respect.

Advantageous Effects

As described above, according to the present disclosure, it is possible to provide a composition for managing pulmonary fibrosis using 4',6,7-trimethoxyisoflavone, and catechol, which suppress EMT by inhibiting the TGF-β1 signal transmission path and also has a pulmonary fibrosis animal model. The composition of the present disclosure may be commercialized as food such as health functional food or medicine such as medicine.

DETAILED DESCRIPTION

Mode for Invention

Hereinbelow, the present disclosure will be described with reference to Examples and Experimental Examples. However, the scope of the present disclosure is not limited to these Examples and Experimental Examples.

<Example> TMF and Catechol Pulmonary Fibrosis Improvement Activity Experiment

1. Reagents and Antibodies

Catechol (1,2-dihydroxybenzene, "BCC") was prepared by purchasing from Sigma Aldrich (St. Louis, Mo.) and then made of 100 mM stock using DMSO. TMF (4',6,7,-TRIMETHOXYISOFLAVONE, "BCT") was prepared by purchasing from INTOFINE Chemical Company, Inc. (located in Hillsborough, N.J., USA)) and used as 100 mM stock using DMSO. Recombinant human TGF-β1 was purchased from Invitrogen (Invitrogen, Life Technologies, CA, USA). Antibodies against E-cadherin, Vimentin, TGF-β, and pSmad2/3 were purchased from Cell Signaling Technology (Boston, MA, USA).

2. Cytotoxicity Assessment

Using the MTT (3-(4,5-dimethylthiazol-2yl)-2,5-diphenyl-2H-tetrazolium bromide) assay was applied to investigate the effect of TMF (BCT) and catechol (BCC) on cell proliferation. $5 \times 10^3$ cells/well were placed in a 96-well plate and incubated for 24 hours at 37° C., 5% CO2 incubator. Then, each sample was treated in each well according to the concentration and then incubated for 24 hours. Then, after washing with PBS, 20 μL of MTT dissolved in PBS and 200 μL of FBS-free DMEM were treated in each well and then incubated for 4 hours under the same conditions after blocking the light. After 4 hours, the culture solution was removed, treated with 200 μL of DMSO (dimethyl sulfoxide), and left at 37° C. for 2 hours, and absorbance was measured at 570 nm using a microplate reader.

Figure 1:
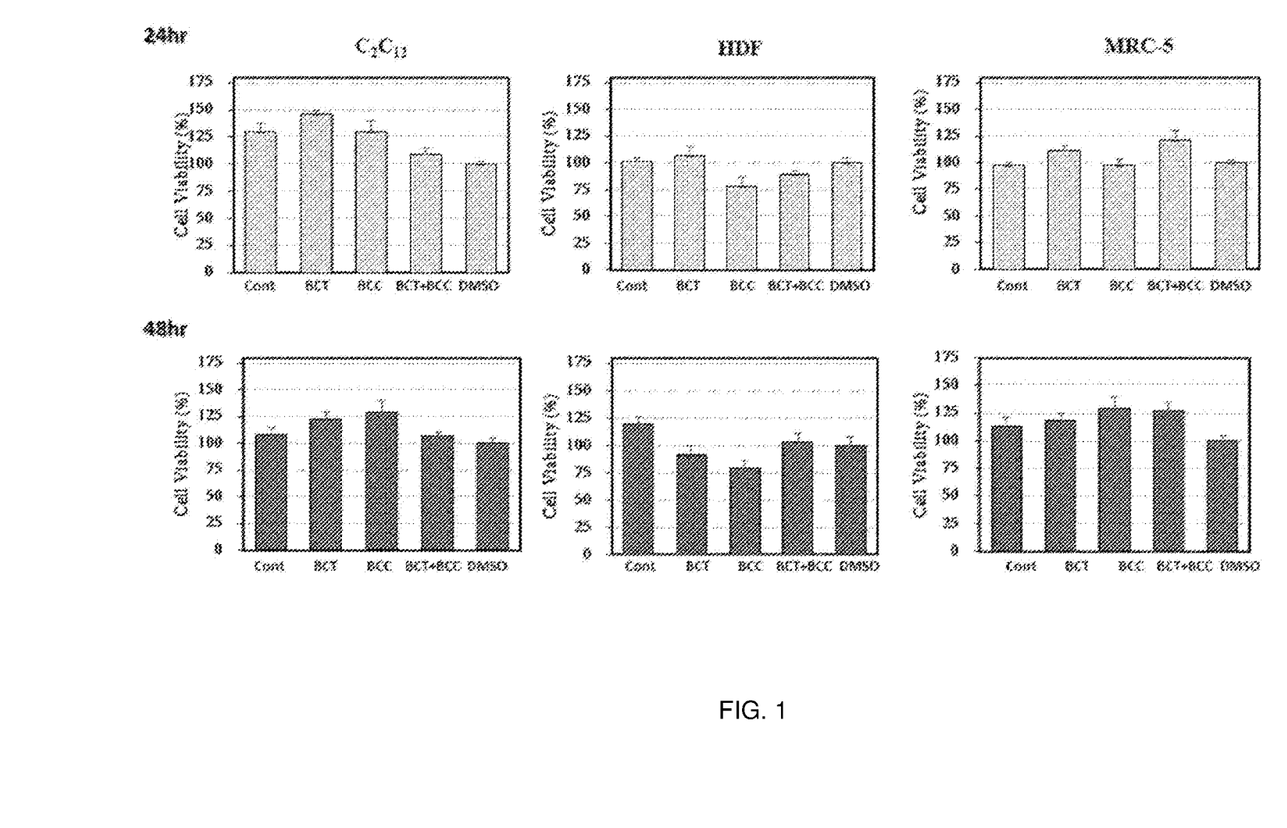
FIG. 1 is a cytotoxicity evaluation result.

The cell viability after 24 hours and 48 hours is shown in FIG. 1 as a percentage compared to the control group, the untreated sample group.

Referring to FIG. 1, BCT and/or BCC did not show any particular cytotoxicity to muscle cells (C2C12), human fibroblasts (HDF, Human Dermal Fibroblast), and human lung fetal cells (MRC-5).

3. Evaluation of EMT Inhibitory Activity Induced by TGF-β1 in Alveolar Epithelial A549 Cells As EMT progresses, the proliferation and movement of epithelial cells increases, cell penetration increases, and cell morphology changes, thereby confirming EMT inhibitory efficacy and evaluating the degree of expression of mechanism-related factors.

3.1 Evaluation of Cell Migration Inhibition Activity

A549 cells were seeded at 1×105 cells in 1 mL per well in a 6-well plate and cultured at 37° C. under 5% CO 2 for 24 hours. After 24 hours, a single cell layer was scratched with a 1 mL tip and a medium containing TGF-β1, TGF-β1, and sample BCT (10 µM) or TGF-β1, and sample BCC (0.5 µM) was added to each well. After culturing for 72 hours, the degree of cell migration was confirmed under a microscope, and images were taken.

Figure 2:
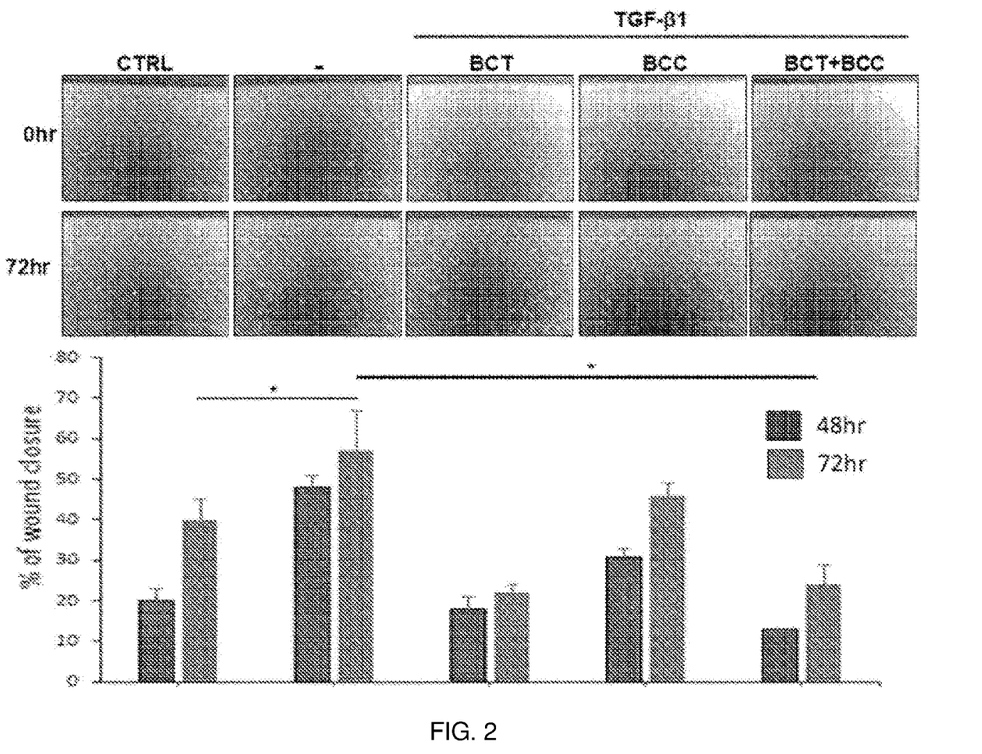
FIG. 2 is a result of cell migration inhibition evaluation.

The results are shown in FIG. 2. Referring to FIG. 2, it may be seen that cell migration is increased in the cells treated with TGF-β1 compared to the control group, and it may be confirmed that the cell migration is decreased when treated with BCT and/or BCC. In particular, when BCT and BCC were treated together, cell migration was significantly reduced.

3.2 Evaluation of Cell Penetration Inhibition Effect

Trans-well inserts (Corning, USA) were coated with Matrigel® (Corning) at 2 mg/L. Dilute A549 cells to about 5×10$^5$/mL in 200 µl of serum-free media, and TGF-β1, TGF-β1 and sample BCT (10 µM) or TGF-β1 and sample BCC (0.5 µM) was added and dispensed into trans-well inserts. The cells were cultured for 24 hours by dispensing a medium containing 10% serum in the receive chambers. After the culture was completed, the cells remaining in the insert were removed, and the cells penetrating the receiving chamber were stained with crystal violet and photographed under a microscope.

Figure 3:
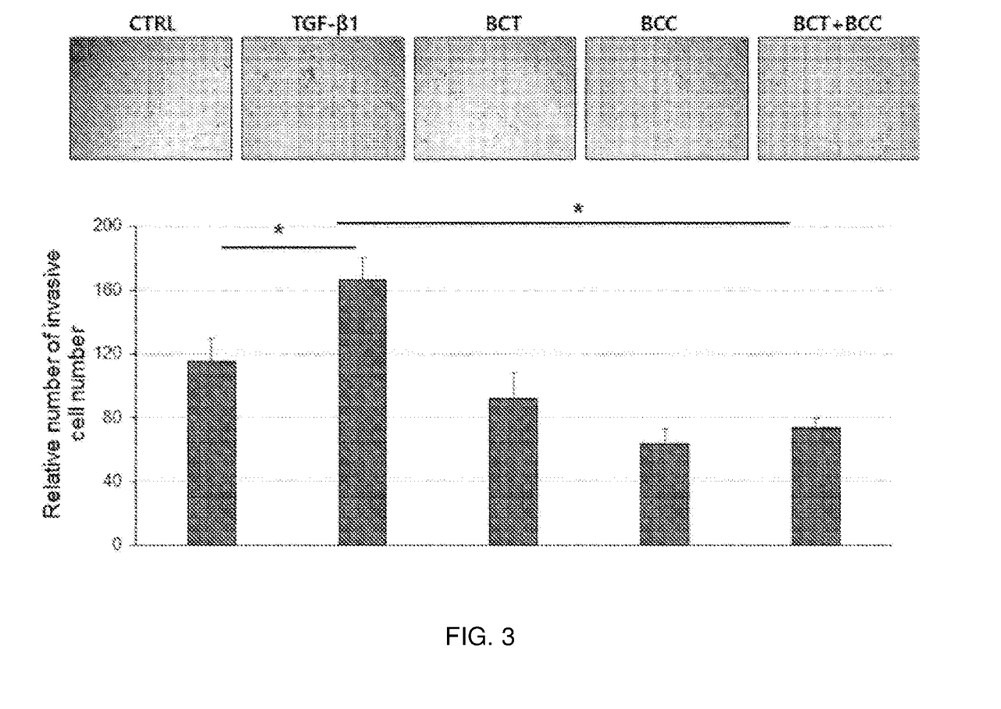
FIG. 3 is a result of cell infiltration inhibition evaluation.

The results are shown in FIG. 3. As may be seen in FIG. 3, in the case of cells treated with TGF-β1 compared to control, the number of cells penetrating into the receiving chamber increased. On the contrary, in the case of cells treated with BCT and/or BCC, the number of cells penetrating into the receiving chamber decreased.

3.3 Confirmation of Expression Changes in EMT Mechanism-Related Factors by Western Blot 2×10$^6$ A549 cells were attached to a 100 mm culture vessel for 24 hours, treated with TGF-β1, TGF-β1 and sample BCT (10 µM) and/or TGF-β1 and sample BCC (0.5 µM)) and cultured. After collecting all of the cultured cells, the cell precipitate was dissolved in a cell lysate RIPA lysis buffer (LPS solution, Korea, Seoul), followed by centrifugation at 13,000 rpm for 20 minutes to obtain a supernatant. The total amount of protein was quantified using the BCA Protein assay kit (Thermo. Scientific, Wilmington, DE, USA) solution. After mixing the protein and 6× sample buffer (1 mL of glycerol, 0.5 mL of β- Mercaptoethanol, 3 mL of 10% SDS, 1.25 mL of 1 M Tris-HCl, 1-2 µg of bromophenol blue), electrophoresis was performed on SDS polyacrylamide gel. After transferring to Nitrocellulose Membrane (Millipore, Billerica, MA, USA) and blocking with 5% non-fat skim milk, protein expression levels of related factors were measured using various antibodies, and whether the protein amount was the same was confirmed using actin. Each of the primary antibodies was diluted and reacted at room temperature for 4 hours, washed 3 times with TBST, the secondary antibody was diluted at 1:5,000 and reacted at room temperature for 30 minutes. After washing with TBST, a band was obtained after light emission with ECL solution (LPS solution, Korea, Seoul).

Figure 4:
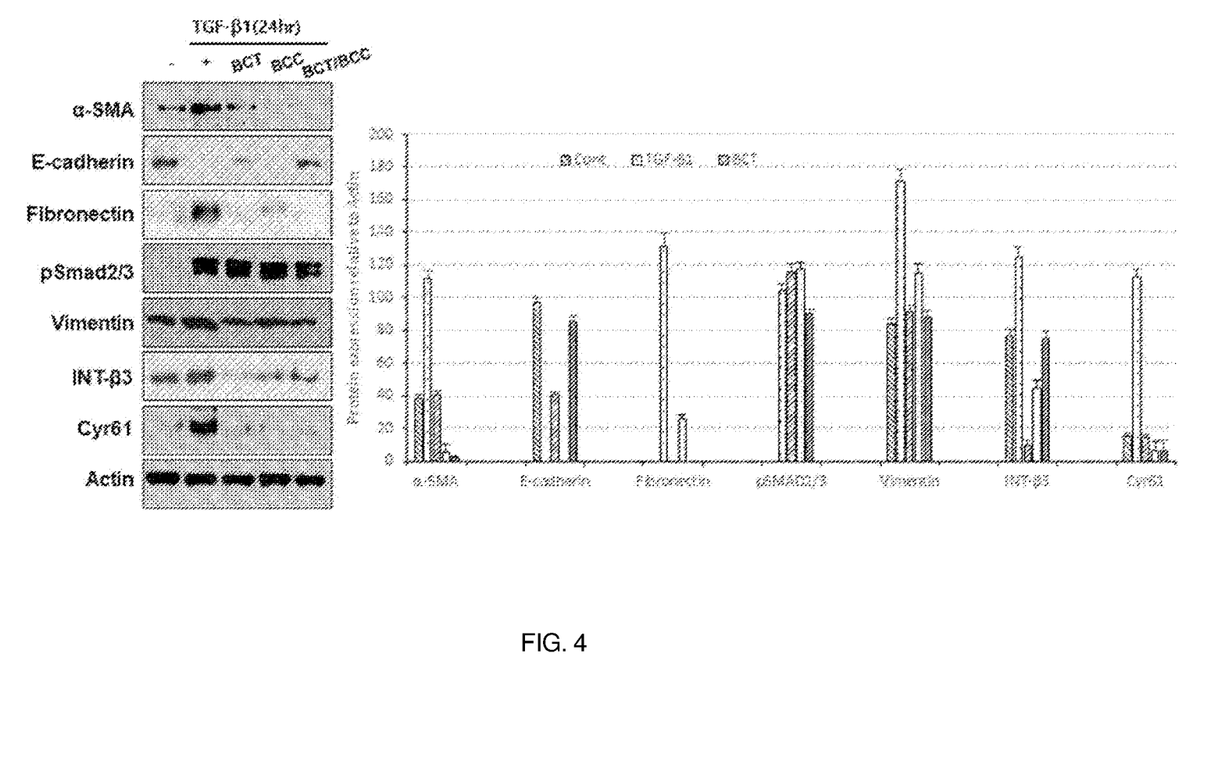
FIGS. 4 and 5 are results of evaluating the expression level of EMT-related mechanism factors by Western blot.
Figure 5:
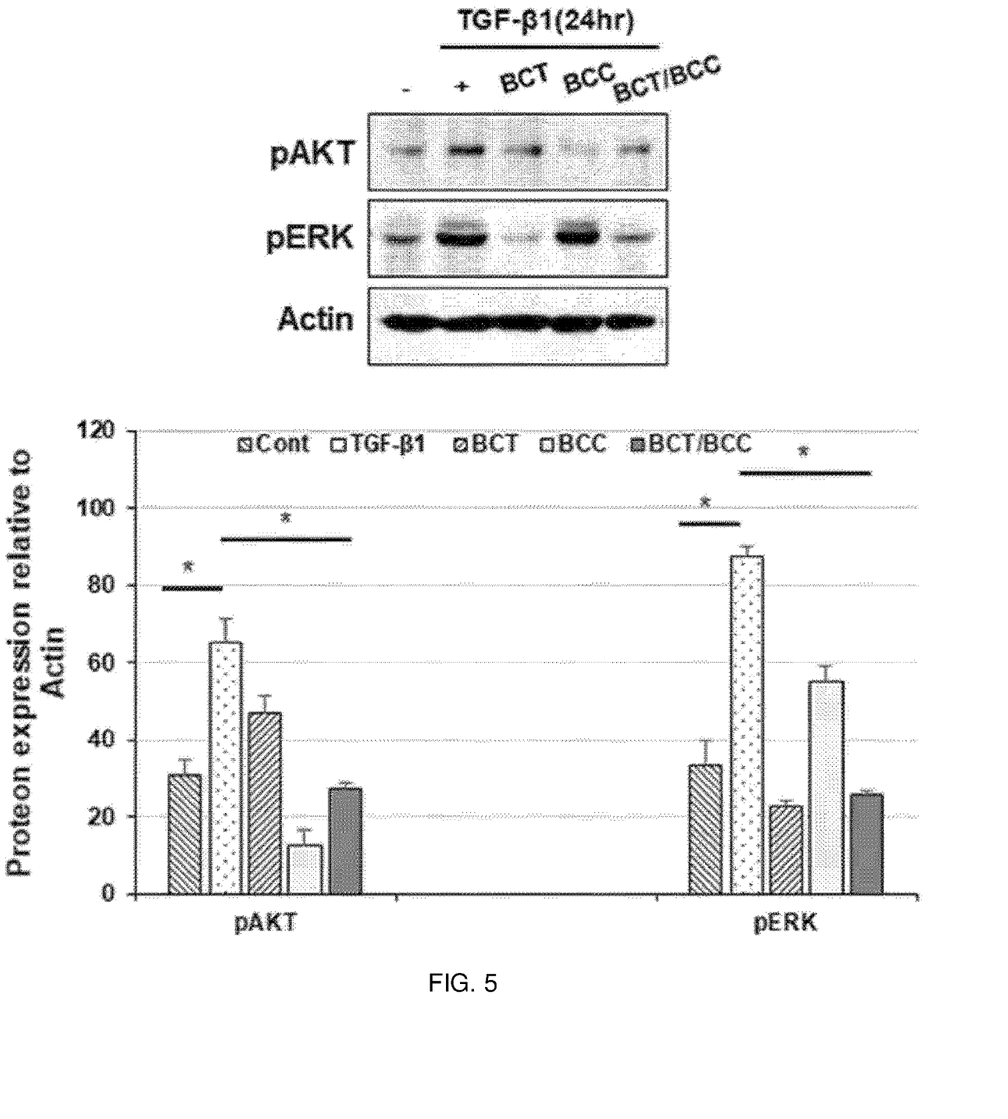

The results are shown in FIG. 4 for the Smad-dependent factor and FIG. 5 for the Smad-independent factor.

Referring to FIG. 4, it may be confirmed that the expression of α-Sma, Vimentin, Fibronectin, SMA2/3, Integrin β3, and Cyr61 increased by TGF-β1 treatment is decreased by BCT and/or BCC treatment. It may be confirmed that the expression of E-cadherin decreased by TGF-β1 treatment was increased by BCT and/or BCC treatment.

Also, referring to FIG. 5, it may be confirmed that the expression of pAKT or pERK increased by TGF-β1 treatment is decreased by BCT and BCC treatment.

3.4 Confirmation of Cell Morphological Changes

A549 cells were seeded on a 60 mm plate at 1×10$^5$ /mL and cultured for 24 hours. Then, 5 mL of a medium containing TGF-β1, TGF-β1 and sample BCT (10 µM) and/or TGF-β1 and sample BCC (0.5 µM) was added to each well and incubated for another 48 hours. After culturing, the cells were checked under a microscope, and images were taken.

Figure 6:
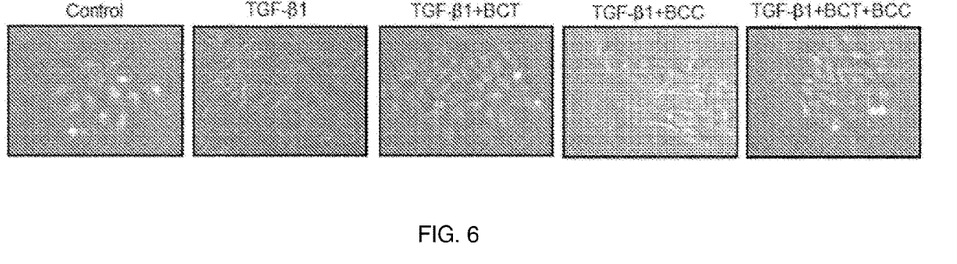
FIG. 6 is a result of cell morphology change evaluation.

The results are shown in FIG. 6. Referring to FIG. 6, although the cell morphology is changed by TGF-β1 treatment, it may be seen that the cell morphology is recovered similarly to the control by BCT and/or BCC treatment.

4. Pulmonary Fibrosis Animal Model Experiment 4.1 Pulmonary Fibrosis Animal Model Production The airways of the mice were incised, and bleomycin (3 mg/kg, BLM) was injected into the airways. After injection, the incision site was sutured with nylon thread, samples of BCT and/or BCC were administered daily 24 hours after bleomycin was injected. Mice were raised to 28 days from the start date of the experiment and sacrificed on day 29 to separate the broncho-alveolar lavage fluid (BALF) and lung tissue and used in further experiments.

Figure 7:
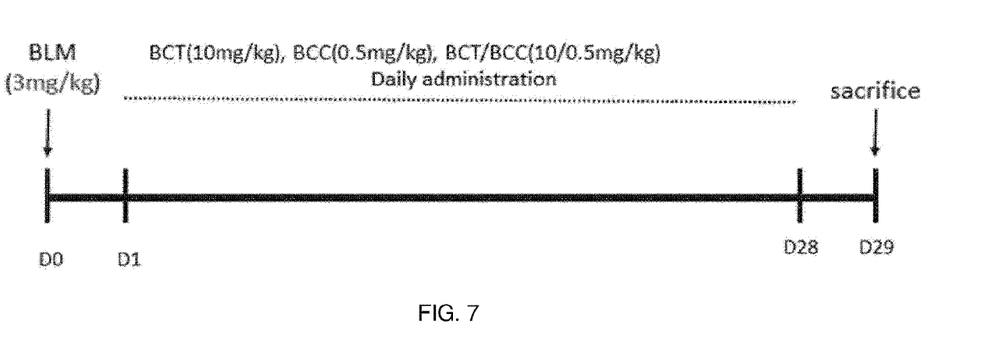
FIG. 7 is a block diagram of an animal model experiment for pulmonary fibrosis.

The configuration diagram of the pulmonary fibrosis animal model experiment is shown in FIG. 7.

4.2 Histopathological Examination

In order to evaluate lung fibrosis, animal models of each control group and experimental group were sacrificed, and the lungs were extracted from these animal models, fixed in 10% neutral buffered formalin (NBF), and then embedded with paraffin to produce tissue sections with a thickness of 2-4 um. After the sections were prepared, Hematoxylin-Eosin staining and Masson's trichrome staining were performed for comparison of histological findings and observed with an optical microscope.

H&E staining was performed to evaluate inflammation and epithelial cell hypertrophy due to lung fibrosis, and Masson's trichrome staining was used to evaluate fibrosis using the following tissue scoring method (Scoring system, Ashcroft score).

TABLE 1

| Degree of fibrosis | grade |
| --- | --- |
| normal lung tissue | 0 |
| minimal inflammatory reactions, hypertrophy of epithelial cells, and collagen deposition fibrosis | 1 |

TABLE 1-continued

| Degree of fibrosis | grade |
|---|---|
| minor inflammatory reactions, hypertrophy of epithelial cells, and collagen deposition fibrosis | 2 |
| medium inflammatory reactions, hypertrophy of epithelial cells, and collagen deposition fibrosis | 3 |
| significant inflammatory reactions, hypertrophy of epithelial cells, and collagen deposition fibrosis | 4 |
| severe inflammatory reactions, hypertrophy of epithelial cells, and collagen deposition fibrosis | 5 |

Figure 8:
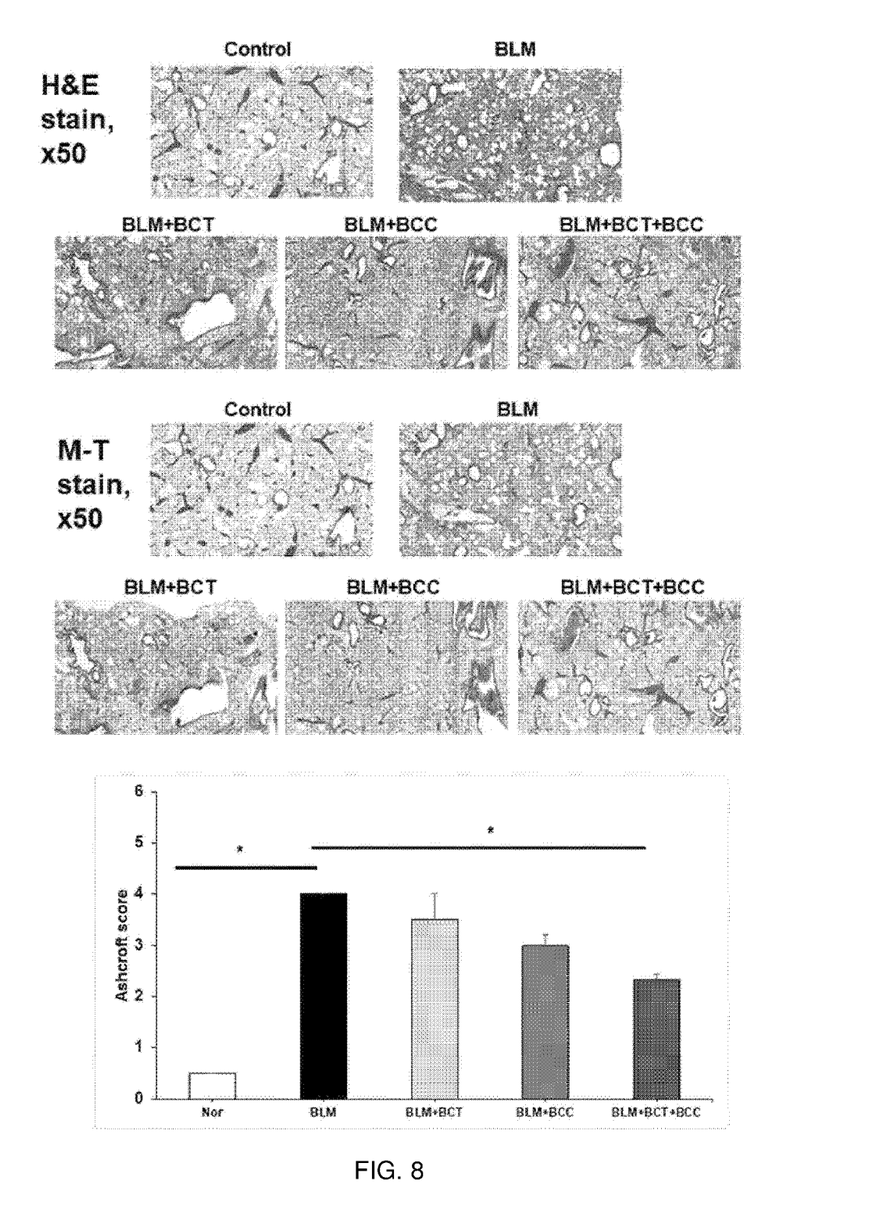
FIG. 8 is a histopathological examination result in a pulmonary fibrosis animal model experiment.

The results are shown in FIG. 8. As confirmed in FIG. 8, compared to the level of fibrotic tissue located in the control group showing normal findings, the damaged fibrosis area displayed in dark red by H&E staining was increased in the lung tissue treated with BLM, but when the BCT and BCC are administered alone or in combination, it may be seen that the size of the increased fibrosis area is reduced. In addition, referring to the graph at the bottom of FIG. 8, which is the result according to the tissue scoring system, it may be confirmed that the size of the fibrosis area was reduced in both the BCT and BCC alone and combined experimental administration groups. In particular, the effect was excellent in the combined administration group.

4.3 Confirmation of Protein Expression Level using Lung Tissue

Animal models of each control group and the experimental group raised for 28 days were sacrificed, and lung tissue samples and serum samples were obtained from these animal models, respectively, and stored in a deep freezer at −70° C. Western blotting was performed for α-Sma, TGF-β1, Fibronectin, and E-cadherin proteins known as major markers of pulmonary fibrosis.

Lung tissue was put into T-PER buffer (lysis buffer, Thermo. Scientific, Wilmington, DE, USA) as a standard of 500 μL per 50 mg of tissue, and the tissue was homogenized using a homogenizer. The homogenized tissue was centrifuged at 13,000 rpm, and the supernatant was used as a sample for Western blot. The concentration of the tissue homogenate was quantified using a BCA Protein assay kit (Thermo. Scientific, Wilmington, DE, USA) solution. After mixing the protein and 6× sample buffer (1 mL of glycerol, 0.5 mL of β-Mercaptoethanol, 3 mL of 10% SDS, 1.25 mL of 1 M Tris-HCl, 1-2 μg of bromophenol blue), electrophoresis was performed on SDS polyacrylamide gel. After transferring to Nitrocellulose Membrane (Millipore, Billerica, MA, USA) and blocking with 5% non-fat skim milk, protein expression levels of related factors were measured using various antibodies, and whether the protein amount was the same was confirmed using actin. Each of the primary antibodies was diluted and reacted at room temperature for 4 hours, washed 3 times with TBST, the secondary antibody was diluted at 1:5,000 and reacted at room temperature for 30 minutes. After washing with TBST, a band was obtained after light emission with ECL solution (LPS solution, Korea, Seoul).

Figure 9:
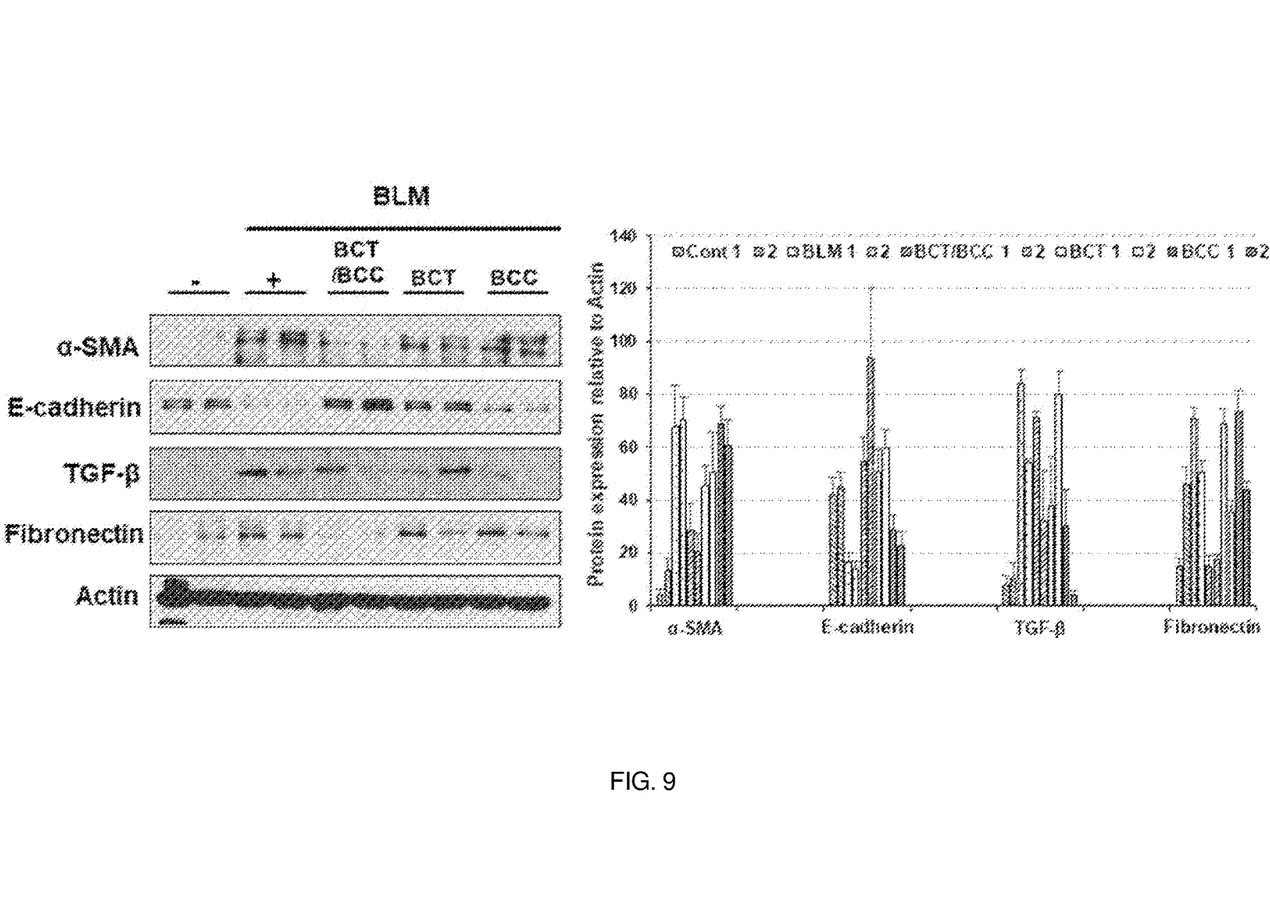
FIG. 9 results from western blotting evaluation of the expression level of EMT-related mechanism factors in the pulmonary fibrosis animal model experiment.

Western blotting results are shown in FIG. 9. Referring to FIG. 9, when pulmonary fibrosis is induced by BLM and BCC and BCT are administered alone or in combination, the expression level of α-SMA, TGF-β1, and fibronectin compared to the experimental group in which pulmonary fibrosis is induced by BLM decreased, and E-cadherin expression increased. In particular, the effect was excellent in the combined administration group.

4.4 Confirmation of Effect on Change in Total Cell Number in Bronchoalveolar Lavage Fluid (BALF)

Pulmonary fibrosis is characterized by an increase in the total number of cells and the percentage of neutrophils in the BALF fluid.

After collecting BALF from each experimental animal group, neutrophils and alveolar macrophages, including total cells, were measured. The method of measuring the total number of cells in BALF, the ratio of neutrophils and alveolar macrophages, etc., is as follows. BALF was mixed with trypan blue in a ratio of 1:1, and then the total number of cells was counted as ×104/BALF 1 mL using a hemocytometer (Fisher Scientific, PA, USA). The prepared BALF was spread on a slide glass and then stained with Diff Quik (manufactured by Sysmex Corporation, USA), the number of neutrophils and alveolar macrophages among a total of 200 cells was counted under a microscope, and the ratio was measured and recorded.

Figure 10:
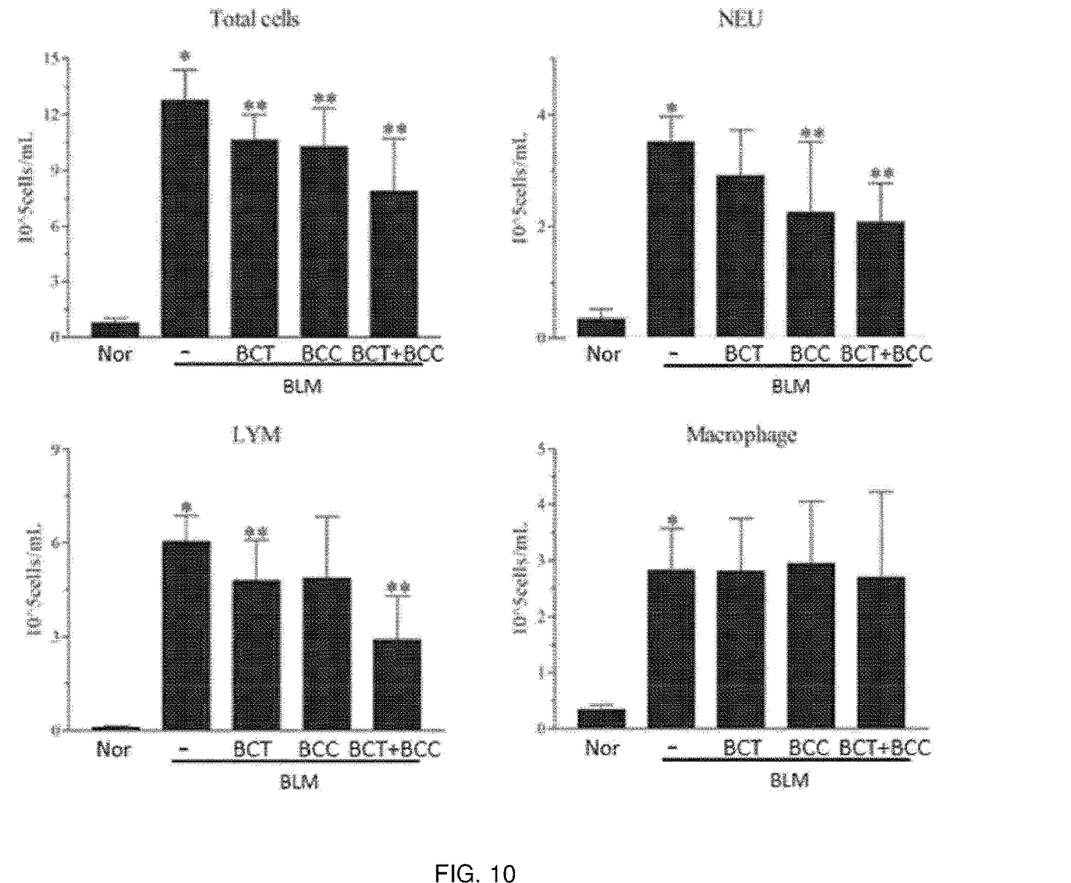
FIG. 10 results from evaluating the change in the total number of cells and neutrophils in the BALF solution.

The results are shown in FIG. 10. In the BLM-administered group, the total number of bacteria, lymphocytes, and neutrophils were increased, and in the case of BCC and BCT alone or in combination, these cell numbers were significantly decreased. Also, here, the effect was excellent, especially in the combined administration group.

What is claimed is:

1. A method for managing pulmonary fibrosis, comprising administering to a subject in need thereof a composition comprising a mixture of 4',6,7-trimethoxyisoflavone and catechol as an active ingredient.
2. The method of claim 1, wherein the composition is a pharmaceutical composition.
3. The method of claim 1, wherein the composition is a food composition.

* * * * *